US006627185B2

(12) United States Patent
Kumar et al.

(10) Patent No.: US 6,627,185 B2
(45) Date of Patent: Sep. 30, 2003

(54) NON-AEROSOL SHAVING GEL FREE OF THICKENING AND GELLING AGENTS

(75) Inventors: Promod Kumar, Midland, MI (US); Jiansheng Tang, Sudbury, MA (US); Kenneth T. Dodd, Upton, MA (US); Karla Leum Stoner, Frederick, MD (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/915,711

(22) Filed: Jul. 26, 2001

(65) Prior Publication Data

US 2003/0021760 A1 Jan. 30, 2003

(51) Int. Cl.7 ................................................ A61K 7/15
(52) U.S. Cl. ......................................... 424/73; 514/944
(58) Field of Search ............................ 424/73; 514/944

(56) References Cited

U.S. PATENT DOCUMENTS

| | | | |
|---|---|---|---|
| 4,917,884 A | 4/1990 | Roberts | 424/73 |
| 4,963,352 A | 10/1990 | Roberts | 424/73 |
| 5,034,220 A | 7/1991 | Helioff et al. | 424/73 |
| 5,279,819 A | 1/1994 | Hayes | 424/73 |
| 5,340,571 A | 8/1994 | Grace | 424/73 |
| 5,451,396 A | 9/1995 | Villars | 424/73 |
| 5,902,574 A * | 5/1999 | Stoner et al. | 424/45 |

* cited by examiner

*Primary Examiner*—Jyothsna Venkat
(74) *Attorney, Agent, or Firm*—Stephan P. Williams

(57) ABSTRACT

The present invention is directed to a non-aerosol shaving composition in the form of a gel, preferably a clear gel. The non-aerosol shaving gel comprises water, an alkanolamine soap, preferably a triethanolamine soap, and a solubilizing agent for the soap, wherein the soap is completely dissolved in the water and the amount of soap and solubilizing agent is sufficient to provide the soap in the hexagonal liquid crystal phase in the composition. The present invention is also directed to an improved shaving method in which a shaving composition of the present invention is applied to an area of skin, then said area is shaved, preferably with a wet razor.

16 Claims, No Drawings

NON-AEROSOL SHAVING GEL FREE OF THICKENING AND GELLING AGENTS

BACKGROUND OF THE INVENTION

This invention relates to non-aerosol shaving gel compositions.

An extensive discussion regarding the formulation of various shaving preparations may be found in *Harry's Cosmeticology*, Seventh Edition, J. B. Wilkinson and R. J. Moore (editors), Chemical Publishing, New York, 1982, pp. 156–189. Currently, the most widely used forms of shaving preparation are the types referred to as instant foams and self-foaming gels (also known as post-foaming gels). U.S. Pat. No. 5,451,396 discloses a post-foaming shave gel that includes a water soluble polymer, such as hydroxyethyl cellulose, as a gelling aid and benzyl alcohol to improve clarity and gel strength. Non-aerosol shaving preparations, both lathering and non-lathering, have been available for decades and come in a variety of forms including bars, sticks, creams, gels and lotions. U.S. Pat. No. 5,340,571 discloses a non-aerosol shaving composition in the form of a clear gel that includes, among other things, potassium myristate and potassium palmitate in a specified ratio and hydroxyethyl cellulose as a gelling aid. U.S. Pat. No. 4,963,352 discloses a non-aerosol shaving composition that includes glyoxal, urea, diethyleneglycol monoethyl ether, fatty acid, alkanolamine, and benzyl alcohol, wherein the alkanolamine to fatty acid ratio is about 1:2 to 1:3.

Generally, the various non-aerosol shaving compositions typically have one or more deficiencies. They can be difficult to deliver and apply to the face. For example, they may be runny, stringy or hard to spread. They can be difficult to lather. And they can be difficult to rinse from the face, hands and razor, particularly when they contain oils, gums, thickening agents or associative thickeners. It would be desirable to provide a non-aerosol shaving composition that did not have these deficiencies.

SUMMARY OF THE INVENTION

The present invention is directed to a non-aerosol shaving composition in the form of a gel, preferably a clear gel. The non-aerosol shaving gel comprises water, an alkanolamine soap, preferably a triethanolamine soap, and a solubilizing agent for the soap, wherein the soap is completely dissolved in the water and the amount of soap and solubilizing agent is sufficient to provide the soap in the hexagonal liquid crystal phase in the composition. The present invention is also directed to an improved shaving method in which a shaving composition of the present invention is applied to an area of skin, then said area is shaved, preferably with a wet razor.

DETAILED DESCRIPTION OF THE INVENTION

The non-aerosol shaving composition of the present invention is in the form of a gel, preferably a clear gel. At a minimum, the shaving gel will include water, an alkanolamine soap, preferably a triethanolamine soap, and a solubilizing agent for the soap. The soap must be completely dissolved in the water and the amount of soap and solubilizing agent must be adjusted to a level sufficient to provide the soap in the hexagonal liquid crystal phase in the composition. When the soap is in the hexagonal liquid crystal form, the shaving composition becomes a stable gel instead of a runny liquid without the need for added thickening or gelling agents. This gel form facilitates ease of application because it will not run off the hands or face and spreads easily. This gel form also facilitates ease of rinsing because the addition of water readily transforms the composition to a less viscous soap phase form. For this reason, the composition preferably will be substantially free of other thickening or gelling agents such as gums, hydroxyalkyl celluloses, polyallyl sucrose copolymers, etc.

The shaving composition will typically comprise, by weight, in addition to water, about 18% to about 28%, preferably about 20% to about 27%, more preferably about 23% to about 26%, of the alkanolamine soap, and about 0.5% to about 6%, preferably about 1% to about 5%, more preferably about 1% to about 3%, solubilizing agent for the soap. As stated previously, the amount of soap and solubilizing agent must be adjusted to a level sufficient to provide the soap in the hexagonal liquid crystal phase in the composition.

Hexagonal liquid crystal phase is a well known concept in surfactant chemistry and means that the soap molecules are arranged in cylinders of indefinite length packed hexagonally in the aqueous continuous phase. This form can be readily seen with a phase contrast, polarizing microscope at magnifications of about 150–200×. When the soap molecules are arranged in this form, the composition becomes a non-flowing gel with a yield viscosity.

The alkanolamine soap may be pre-formed or, more typically, may be prepared in situ. It is prepared by the neutralization of a fatty acid (or a mixture of fatty acids) with an alkanolamine. The amount of fatty acid will range from about 12% to about 18%, preferably about 14% to about 16%. The amount of alkanolamine will be sufficient (typically a slight molar excess) to completely neutralize the fatty acid so that there is essentially no free fatty acid. Thus, the amount of alkanolamine will fall within the range of about 7.9% to about 11.9%, preferably about 8.8% to about 10.5%. Typically the composition will have a pH between about 7 and about 8.5, more typically between about 7.2 and about 8.0. Fatty acids which may be used include the $C_{10}$ to $C_{20}$, preferably $C_{12}$ to $C_{18}$, more preferably $C_{14}$ to $C_{16}$, fatty acids. Typical fatty acids include lauric, oleic, coconut oil, myristic, palmitic and stearic acid and mixtures thereof. The preferred fatty acids are myristic and palmitic and mixtures thereof, with myristic being most preferred. Generally, the higher carbon chain fatty acids, such as stearic acid, are somewhat less preferred because their soaps are less soluble and require higher amounts of the solubilizing agent. The alkanolamine may be any suitable mono-, di- or tri-alkanolamine having from 2 to 6 carbon atoms in the alkanol chain(s). Preferably the alkanolamine will be monoethanolamine, diethanolamine or triethanolamine, with triethanolamine being most preferred.

The solubilizing agent is a material which helps to solubilize the soap component in water and assists in the formation and stability of the hexagonal crystal phase. The solubilizing agent is a bipolar molecule with a hydrophobic hydrocarbon tail, such as a benzyl or phenyl or medium alkyl moiety, and a non-ionic hydrophilic head, such as hydroxyl (—OH), glycol, or carboxylate. Typical solubilizing agents may include, for example, benzyl alcohol, phenoxyethanol, benzyl glycol, phenethyl alcohol, benzyl acetate, benzyl butyrate, benzyl glycoate, 2-ethylhexyl salicylate, 2-phenoxypropanol, 1-butanol, pentanol, hexanol, heptanol, octanol, hexylene glycol, butoxyethanol, butoxyisopropanol, butoxyethanol acetate, nonoxynols, fatty alcohol polyglycol ethers, alkylphenol polyglycol ethers, alkylphenol ethoxylates, and mixtures thereof. The preferred solubilizing agent is selected from benzyl alcohol, hexylene glycol, phenoxyethanol, butoxyisopropanol and mixtures of at least two of these, with benzyl alcohol being most preferred. The amount of solubilizing agent should be sufficient to solubilize the soap component and allow it to form the hexagonal crystal phase. Typically it will comprise about 0.5% to about 6%, preferably about 1% to about 4%, more preferably about 1% to about 3%, of the composition.

Although not necessary to forming a useful shaving composition, other cosmetic ingredients may be advantageously added to improve the application aesthetics and/or achieve other shave benefits. For example, the composition may include one or more of the following components: beard wetting agents (e.g., non-ionic and/or anionic surfactants), skin conditioning agents (e.g., vitamins A, C and E, aloe, allantoin, panthenol, alpha-hydroxy acids, phospholipids, triglycerides, botanical oils, amino acids), cleansing agents, lathering agents, foam boosters, emollients, humectants (e.g., glycerin, sorbitol, propylene glycol), lubricants, fragrances, colorants, antioxidants, preservatives, etc.

The shaving composition may advantageously include from 0% to about 6%, preferably from about 1% to about 5%, of a non-ionic surfactant and/or from 0% to about 6%, preferably from about 1% to about 3%, of an anionic surfactant. Preferably the surfactant(s) will have an HLB of 14 or higher, more preferably 15 or higher. Suitable non-ionic surfactants include the polyoxyethylene ethers of fatty alcohols, acids and amides, particularly those having 10 to 20, preferably 12 to 18, carbon atoms in the fatty moiety and about 8 to 60, preferably 10 to 30, ethylene oxide units. These include, for example, Oleth-20, Steareth-21, Ceteth-20, and Laureth-23. Other non-ionic surfactants include the polyoxyethylene ethers of alkyl substituted phenols, such as Nonoxynol-4 and Nonoxynol-20, fatty alkanolamides such as Lauramide DEA and Cocamide MEA, polyethoxylated sorbitan esters of fatty acids, such as Polysorbate-20, lauryl polyglucoside, sucrose laurate, and polyglycerol 8-oleate. Suitable anionic surfactants include, for example, the sodium, potassium, ammonium and substituted ammonium salts (such as the mono-, di- and triethanolamine salts) of $C_8$–$C_{22}$, preferably $C_{12}$–$C_{18}$, alkyl sulfates (e.g. sodium lauryl sulfate, ammonium lauryl sulfate), alkyl sulfonates (e.g. ammonium lauryl sulfonate), alkylbenzene sulfonates (e.g. ammonium xylene sulfonate), acyl isethionates (e.g. sodium cocoyl isethionate), acyl lactylates (e.g. sodium cocoyl lactylate), $C_8$–$C_{22}$, preferably $C_{12}$–$C_{18}$, alkyl ether sulfates (e.g. sodium laureth (23) sulfate, ammonium laureth sulfate), and $C_8$–$C_{22}$, preferably $C_{12}$–$C_{18}$, acyl sarcosinates (e.g. sodium lauroyl sarcosinate). The addition of one or more surfactants can improve the stability of the formulation over a wider temperature range. The inclusion of both a non-ionic surfactant and an anionic surfactant is particularly advantageous. It is especially preferred to include both a fatty alkyl ether sulfate (e.g. sodium laureth (23) sulfate) and a fatty acyl sarcosinate (e.g. sodium lauroyl sarcosinate), particularly in an approximately 1:1 weight ratio.

The shaving composition may optionally include a humectant such as glycerin or sorbitol, typically in an amount of about 3% to 10%. The shaving composition may also include one or more polymers to increase lubricity and/or improve foam capacity or stability. Preferably the amount of polymer(s) should be kept to a minimum (i.e., <1%, preferably 0.1 to 0.5%) so as not to interfere with rinsing. Suitable polymers include polyethylene oxides of molecular weight of about one million or higher, typically up to about five million, poyacrylamides of molecular weight of about 500,000 to about five million, polyvinylpyrrolidones of molecular weight of about 500,000 to about three million, and copolymers of (meth)acrylamide-co-diallyldimethylammonium chloride-co-acrylic acid such as Polyquaternium-39.

The shaving compositions of the present invention may be packaged in any suitable dispenser normally used for dispensing non-aerosol shaving gels or creams. These include collapsible tubes, pump or squeeze containers, and pressure-type dispensers with a barrier to separate the shaving composition from the propellant required for expulsion.

The invention may be further described by the following examples in which all parts and percentages are by weight.

EXAMPLES 1 to 5

| Ingredient | Weight Percent | | | | |
| --- | --- | --- | --- | --- | --- |
| | Ex. 1 | Ex. 2 | Ex. 3 | Ex. 4 | Ex. 5 |
| Myristic Acid | 9.00 | 15.00 | 15.00 | 12.00 | 12.00 |
| Palmitic Acid | 3.00 | | | 3.00 | 3.00 |
| Stearic Acid | 3.00 | | | | |
| Triethanolamine (99%) | 9.40 | 9.99 | 9.99 | 9.79 | 9.79 |
| Benzyl Alcohol | 1.00 | | 1.00 | 1.00 | 1.00 |
| Hexylene Glycol | | | 1.00 | 0.75 | 0.75 |
| Phenoxyethanol | | | 1.00 | 1.00 | 1.00 |
| Butoxyisopropanol | | 5.00 | | | |
| Lauramide DEA | | 2.25 | 2.25 | 2.25 | 1.80 |
| Oleth-20 | | 1.00 | 1.00 | 2.00 | |
| Glycerin | | 5.00 | 5.00 | 5.00 | 5.00 |
| Sodium Lauroyl Sarcosinate | | 2.00 | | 1.00 | 3.00 |
| Sodium Laureth (23) Sulfate | | 2.00 | | 1.00 | 3.00 |
| PEG-23M | | | | 0.20 | 0.20 |
| Polyquaternium-39 | | 0.40 | | | |
| Aloe | | 0.005 | | 0.005 | 0.005 |
| Fragrance/dye | | 0.85 | 0.85 | 1.105 | 1.105 |
| Water | q.s. | q.s. | q.s. | q.s. | q.s. |

The above-described compositions are made in the following manner: The polyethylene oxide (if present) is added to water and mixed until completely dissolved (about 30 min.). The mixture is then heated to 80° C. and the fatty acids and other surfactants (if present) are added and mixed until melted. Glycerin (if present) is added, then the triethanolamine is added and mixed until a clear solution is formed. Polyquaternium-39 (if present) is added and mixed until uniformly dispersed. After cooling the solution to 40° C., the remaining ingredients are added.

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. A non-aerosol shaving composition in the form of a gel comprising water, about 20% to about 27% of an alkanolamine soap, and about 0.5% to about 6% of a solubilizing agent for the soap, wherein the soap is completely dissolved in the water and is in the hexagonal liquid crystal phase, and wherein the solubilizing agent is a mixture of two or more of benzyl alcohol, phenoxyethanol, hexylene glycol, or butoxyisopropanol.

2. A non-aerosol shaving composition in the form of a gel comprising water, about 23% to about 26% of an alkanolamine soar, and about 0.5% to about 6% of a solubilizing agent for the soap, wherein the soap is completely dissolved in the water and is in the hexagonal liquid crystal phase, and wherein the composition is free of thickening or gelling agents.

3. The shaving composition of claim 2 comprising 23% to 26% of the alkanolamine soap and about 1% to about 5% of the solubilizing agent.

4. The shaving composition of claim 1, 2 or 3 additionally comprising from 0% to about 6% of a non-ionic surfactant and from 0% to about 6% of an anionic surfactant.

5. The shaving composition of claim 3 additionally comprising from about 1% to about 5% of a non-ionic surfactant and from about 1% to about 3% of an anionic surfactant.

6. The shaving composition of claim 5 wherein the non-ionic surfactant and the anionic surfactant each have an HLB of 14 or higher.

7. The shaving composition of claim 6 additionally comprising a humectant.

8. The shaving composition of claim 7 wherein the humectant is glycerin.

9. The shaving composition of claim 2 wherein the alkanolamine soap comprises a triethanolamine soap of myristic acid, palmitic acid, or stearic acid or a mixture of two or more of these fatty acids.

10. The shaving composition of claim 9 wherein the solubilizing agent is selected from benzyl alcohol, phenoxyethanol, benzyl glycol, phenethyl alcohol, benzyl acetate, benzyl butyrate, benzyl glycoate, 2-ethylhexyl salicylate, 2-phenoxypropanol, 1-butanol, pentanol, hexanol, heptanol, octanol, hexylene glycol, butoxyethanol, butoxyisopropanol, butoxyethanol acetate and mixtures of two or more of these.

11. The shaving composition of claim 6 wherein the alkanolamine soap comprises a triethanolamine soap of myristic acid, palmitic acid, or stearic acid or a mixture of two or more of these fatty acids.

12. The shaving composition of claim 11 wherein the solubilizing agent is selected from benzyl alcohol, phenoxyethanol, hexylene glycol, butoxyisopropanol and mixtures of two or more of these.

13. The shaving composition of claim 6 wherein the alkanolamine soap comprises a triethanolamine soap of myristic acid, palmitic acid or a mixture thereof.

14. The shaving composition of claim 13 wherein the solubilizing agent is selected from benzyl alcohol, phenoxyethanol, hexylene glycol, butoxyisopropanol and mixtures of two or more of these.

15. A method of shaving comprising applying to an area of skin a non-aerosol shaving composition and shaving said area of skin, wherein said non-aerosol shaving composition is in the form of a gel and comprises water, about 23% to about 26% of an alkanolamine soap, and about 0.5% to about 6% of a solubilizing agent for the soap, wherein the soap is completely dissolved in the water and is in the hexagonal liquid crystal phase, and wherein the composition is free of thickening or selling agents.

16. A method of shaving comprising applying to an area of skin a non-aerosol shaving composition and shaving said area of skin, wherein said non-aerosol shaving composition is a shaving composition according to claim 3, 5, 6, 7, 8, 9, 10, 11, 12, 13 or 14.

* * * * *